United States Patent [19]

Walsgrove et al.

[11] Patent Number: 4,950,765

[45] Date of Patent: Aug. 21, 1990

[54] PROCESS

[75] Inventors: Timothy C. Walsgrove, Tunbridge Wells; Paul Oxley, Pembury, both of England

[73] Assignee: Smith Kline & French Laboratories Limited, Welwyn Garden City, England

[21] Appl. No.: 88,774

[22] Filed: Aug. 24, 1987

[30] Foreign Application Priority Data

Aug. 30, 1986 [GB] United Kingdom ............... 8621040

[51] Int. Cl.$^5$ .............................................. C07D 209/40
[52] U.S. Cl. .................................................. 548/486
[58] Field of Search ....................................... 548/486

[56] References Cited

U.S. PATENT DOCUMENTS 4,452,808  6/1984  Gallagher, Jr. ....................... 548/486

FOREIGN PATENT DOCUMENTS 113964  10/1986  European Pat. Off. .

OTHER PUBLICATIONS

S. Geiger et al., Bull. Chim. Soc. France, No. 1, pp. 390–394 (1968).
RajanBabu et al, J. Org. Chem., 51:1704–1712 (1986).
Wright et al, J. Am. Chem. Soc., 78:221–224 (1956).
Davis et al, J. Med. Chem., 16:1043–1045 (1973).
Brieger et al, Chem. Reviews, 74:567–580 (1974).
Houben Weye, Methode der Organischen Chemie, vol. XI/1, 1957, George Thieme Verlag, Stuttgart, DE; pp. 454–457, 367.
Entwistle et al, J. Chem. Soc., Perkins Trans. I:443–444 (1977).
Ayyangar et al, Synthesis, 640–643 (1981).

Primary Examiner—Mary E. Ceperley
Attorney, Agent, or Firm—Mary E. McCarthy; Stuart R. Suter; Edward T. Lentz

[57] ABSTRACT

This invention relates to a catalytic transfer hydrogenation process using water as a solvent in the preparation of substituted indolinone derivatives.

8 Claims, No Drawings

PROCESS

PROCESS

The present invention relates to an improved process for the preparation of substituted indolinone derivatives. Such compounds are described in EP No. 0113964A as being useful in cardiovascular therapy.

EP No. 0113964A describes a process for the preparation os substituted indolinone derivatives which comprises reduction, by catalytic hydrogenation, of an 2-nitrophenyl acetic acid precusor followed by spontaneous cyclisation of the intermediate so formed. The hydrogenation is carried out in an organic solvent, for example ethanol under low to moderate pressure.

It has now unexpectedly been found that the reduction can be carried out by transfer hydrogenation in water as a solvent to produce the desired substituted indolinones in high yield and high purity. The quality and yields of product are particularly important when preparing compounds on a large scale for therapeutic use.

The present invention therefore provides a process for the preparation of a compound of structure (I)

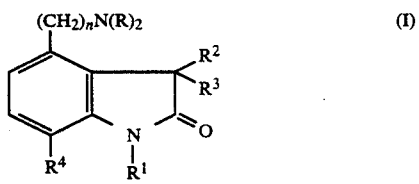

in which,
each group R is hydrogen, $C_{1-6}$alkyl, $C_{3-6}$allyl, phenyl$C_{1-6}$alkyl or 4-hydroxyphenyl$C_{1-6}$alkyl;
$R^1$, $R^2$ and $R^3$ are hydrogen or $C_{1-6}$alkyl;
$R^4$ is hydrogen or hydroxy; and
n is 1 to 3
or a pharmaceutically acceptable salt thereof, which comprises reduction of a compound of structure (II)

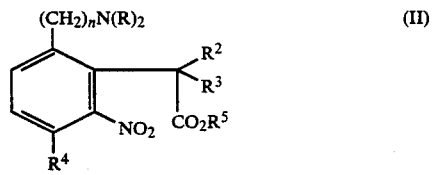

in which R, $R^2$ to $R^4$ and n are as described for structure (I) and $R^5$ is hydrogen or a cation, followed by cyclisation of the intermediate so formed, and optionally alkylating to form a compound in which $R^1$ is $C_{1-6}$alkyl and, optionally, forming a pharmaceutically acceptable salt, characterised in that the reduction of the compound of structure (II) is carried out by catalytic transfer hydrogenation in water as a solvent.

Suitably, the process can be used to prepare compounds of structure (I) in which each R is $C_{1-6}$alkyl; preferably n-propyl. In particular the process can be used to prepare 4-(2-dipropylaminoethyl)-2-indolinone or the hydrochloride salt thereof.

Suitably, the reaction is carried out on compounds of structure (II) in which $R^5$ is hydrogen, that is to say the free acid precursor; preferably the reaction is carried out on compounds of structure (II) in which $R^5$ is a cation, that is to say the salt of the acid. Suitably the cation is an alkali metal cation, preferably sodium ($Na^+$).

The reduction is carried out by hydrogenation over a suitable catalyst in the presence of a hydrogen donor. Suitable catalysts include, for example, Raney Nickel or noble metal catalysts such as platinum or palladium on carbon. Suitable hydrogen donors include for example hydrazine hydrate or sodium hypophosphite. Preferably, the reduction is carried out by hydrogenation over a noble metal catalyst in particular, palladium on carbon, in the presence of hydrazine hydrate.

Suitably, the reaction is carried out at a temperature of between 0° and 50°, preferably at about ambient temperature or just above, that is to say 15° to 25°.

Preferably, therefore, the reduction is carried out by hydrogenation over a palladium on carbon catalyst in the presence of hydrazine hydrate at 15° to 25° in water as a solvent.

It has been found that when the reduction of a compound of structure (II) the following cyclisation reaction are carried out in accordance with the present invention, the compounds of structure (I) are produced in high yields (approximately 80–85%) and in very high purity >99% by HPLC).

EXAMPLE 1

Preparation of 4-(2-dipropylaminoethyl)-2-indolinone hydrochloride.

1-2-(2-di-n-propylaminoethyl)-6-nitrophenyl)acetic acid hydrochloride (1.13 kg, 3 moles) was added to a solution of sodium hydroxide (240 g, 6 moles) in water (6 L). 10% palladium on carbon (225 g) was added and the mixture stirred for 20 minutes whilst cooling to bring the temperature to 20°.

The flask was purged with nitrogen and hydrazine hydrate (300 g, 6 moles) added cautiously. The temperature of the mixture began to rise and cooling was used to maintain the temperature to between 16° and 22° during the addition. The addition was completed after about 1 hour and the mixture stirred for 1.15 hours at about 20°.

The reaction mixture was filtered and the filter cake washed with water (600 ml). The filtrate was then acidified with concentrated hydrochloric acid (600 ml), and the resultant mixture heated to 70°. The flask was then removed from the heat source and cooled on an ice-water bath and left to stand at ambient temperature overnight.

Sodium hydroxide (150 g) was added to the mixture with stirring to give a solution of approximately pH 9. The product was extracted with ethyl acetate (1.4 L, then 2×800 ml). The combined extracts were dried (MgSO$_4$, 40 g), filtered and added to n-propanol (13 L). Hydrochloric acid (300 ml) was added with stirring and after 5 minutes a precipitate formed.

The mixture was cooled to 10° (ice/salt) and allowed to stand at 10° for 1 hour. The resultant solid was then filtered off, washed with n-propanol (2×500 ml) and dried to give the title compound as an off-white solid, 735 g, 82.5%, m.p. 245°–247°.

What is claimed is:

1. A process for the preparation of a compound of structure (I)

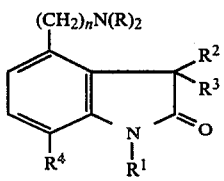

in which,
  each group R is hydrogen, $C_{1-6}$alkyl, $C_{3-6}$allyl, phenyl$C_{1-6}$alkyl or 4-hydroxyphenyl$C_{1-6}$alkyl;
  $R^1$, $R^2$ and $R^3$ are hydrogen or $C_{1-6}$alkyl;
  $R^4$ is hydrogen or hydroxy; and
  n is 1 to 3
or a pharmaceutically acceptable salt thereof, which comprises reduction of a compound of structure (II)

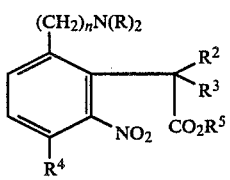

in which R, $R^2$ to $R^4$ and n are as described above and $R^5$ is hydrogen or a cation, followed by cyclisation of the intermediate so formed, and optionally, alkylating to form a compound of structure (I) in which $R^1$ is $C_{1-6}$alkyl and, optionally, forming a pharmaceutically acceptable salt thereof, characterised in that the reduction of the compound of structure (II) is carried out by catalytic transfer hydrogenation in water as a solvent in the presence of a hydrogen donor selected from hydrazine hydrate or sodium hypophosphite.

2. A process according to claim 1 in which both groups R are $C_{1-6}$alkyl.

3. A process according to claim 2 in which the compound of structure (I) is 4-(2-dipropylaminoethyl)-2-indolinone or the hydrochloride salt thereof.

4. A process according to any one of claims 1 to 3 in which the transfer reduction is carried out by hydrogenation over a noble metal catalyst in the presence of hydrazine hydrate.

5. A process according to claim 4 in which the noble metal catalyst is palladium on carbon.

6. A process according to any one of claims 1 to 3 in which the reaction is carried out at a temperature of about 20°.

7. A process according to any one of claims 1 to 3 in which $R^5$ is $Na^+$.

8. A process according to claim 5 in which the reaction is carried out at a temperature of about 20° and in which $R^5$ is $Na^+$.

* * * * *